US012502302B1

(12) United States Patent
Cruz, Jr.

(10) Patent No.: US 12,502,302 B1
(45) Date of Patent: Dec. 23, 2025

(54) SHOULDER SUPPORT APPARATUS

(71) Applicant: Dewey H. Cruz, Jr., Oceano, CA (US)

(72) Inventor: Dewey H. Cruz, Jr., Oceano, CA (US)

( * ) Notice: Subject to any disclaimer, the term of this patent is extended or adjusted under 35 U.S.C. 154(b) by 0 days.

(21) Appl. No.: 18/805,764

(22) Filed: Aug. 15, 2024

(51) Int. Cl.
*A61F 5/37* (2006.01)

(52) U.S. Cl.
CPC .................................. *A61F 5/3746* (2013.01)

(58) Field of Classification Search
CPC ..................................................... A61F 5/3746
See application file for complete search history.

(56) References Cited

U.S. PATENT DOCUMENTS 6,306,111 B1 10/2001 Dean
7,785,281 B2 8/2010 Scott
8,997,267 B2 * 4/2015 Skottheim .......... A41D 13/0518 2/463
10,646,769 B1 5/2020 Farris
11,058,569 B2 7/2021 Fair
11,179,259 B2 11/2021 Matthews
2015/0216700 A1 8/2015 Paparella
2023/0276871 A1 * 9/2023 Brown ............... A41D 13/0512 2/462

FOREIGN PATENT DOCUMENTS

WO WO-2008105671 A1 * 9/2008 ........... A61F 13/146

* cited by examiner

*Primary Examiner* — Tarla R Patel

(74) *Attorney, Agent, or Firm* — TMB Law; Timothy M. Brown

(57) ABSTRACT

The invention provides a shoulder support apparatus having a torso engaging body and shoulder securing elements, each made from an elastic material, that stabilize and support the shoulders of a user. The shoulder securing elements are adjustable to permit a user to achieve a desired level of shoulder stabilization and support. The apparatus finds use in supporting and stabilizing an injured shoulder to make shoulder movements less painful, promote shoulder rehabilitation, and to prevent further injury.

1 Claim, 6 Drawing Sheets

SHOULDER SUPPORT APPARATUS

FIELD OF THE INVENTION

The invention is in the field of apparatuses and methods for orthopedic support and stabilization of the human body. More particularly, the invention relates to an apparatus and method for the orthopedic support and stabilization of the human shoulder.

BACKGROUND OF THE INVENTION

Due to its bone structure and extensive range of possible movements, the shoulder is an intricate portion of a human body. The shoulder comprises three bones: a clavicle, a scapula, and a humerus. The three bones then form three joints: a glenohumeral joint, an acromioclavicular joint, and a sternoclavicular joint. Several major muscles attach to the scapula, the clavicle, or the humerus and are capable of controlling the movement of one or more of the joints. With a wide array of possibilities for movement of the shoulder, athletes and layusers alike frequently use these joints and are at risk for an even wider array of shoulder injuries. It has been reported by the American Academy of Orthopedic Surgeons that approximately four million people in the United States each year seek medical treatment for shoulder injuries such as sprains, strains, tears, dislocations, and the like. When such an injury occurs, for example, with an acromioclavicular (AC) separation, standard treatment options include rest and non-use of the shoulder, which often involves placing the arm corresponding to the injured shoulder in a sling.

After an individual's recuperation of the shoulder has reached a point where a sling is no longer required or in use, the shoulder remains susceptible to further injury. Moreover, common movements of the shoulder remain painful and weak. What is needed in the art therefore is an orthopedic stabilization device that supports the shoulder without the use of a sling while permitting a user to execute common shoulder movements.

SUMMARY OF THE INVENTION

The invention provides an apparatus and method for providing orthopedic support and stabilization of the shoulder. The apparatus incorporates a torso engaging body having a combination of one or more shoulder supporting elements that provide inward and upward compressive force to the shoulder of the user. The apparatus finds use in supporting and stabilizing the shoulder without the use of a sling. However, a sling may be used with the inventive apparatus if desired by a user.

Figure 1:
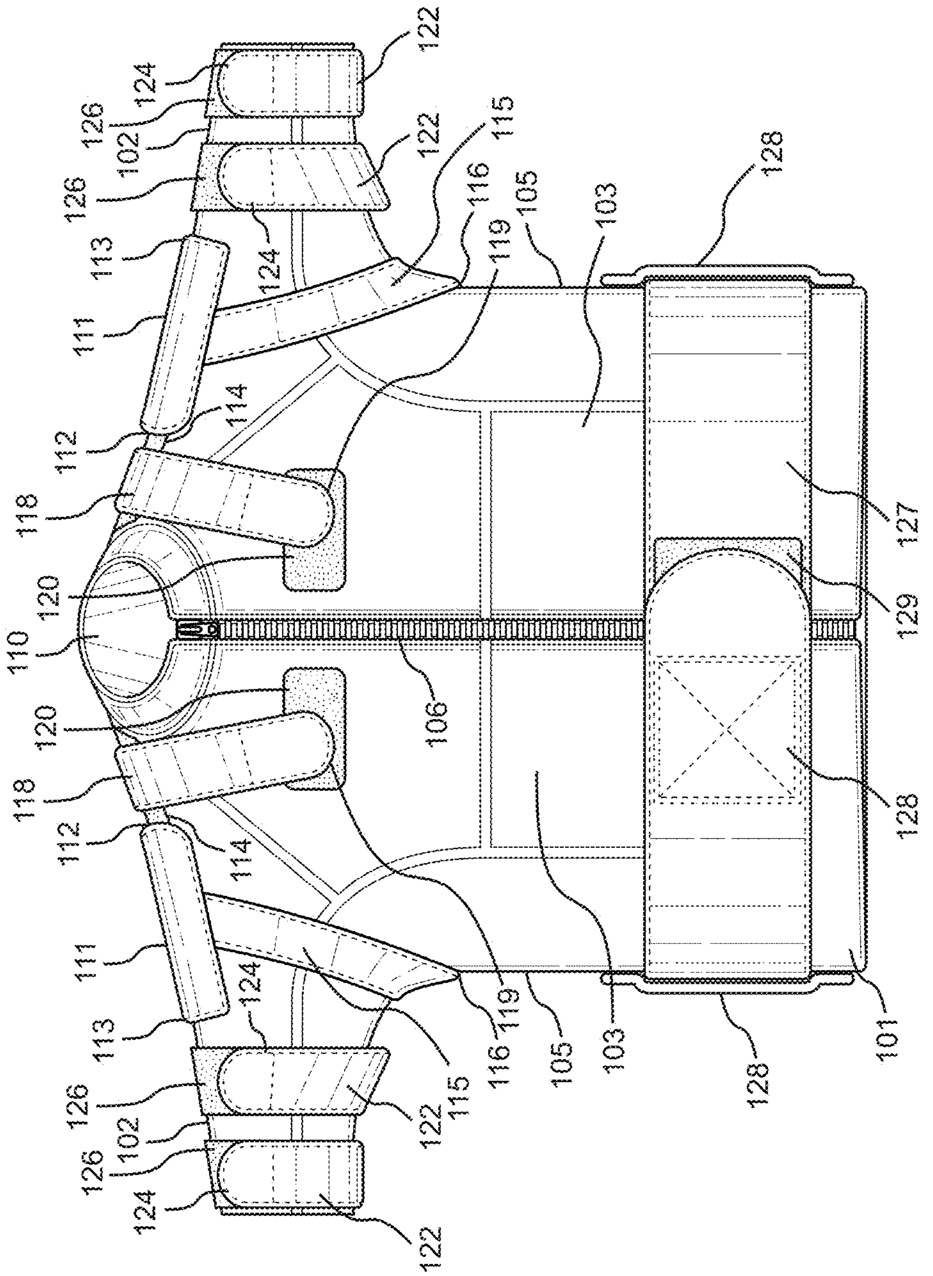
FIG. 1 shows a front view of an embodiment of the inventive shoulder support apparatus with securing elements in their releasably connected state.
Figure 2:
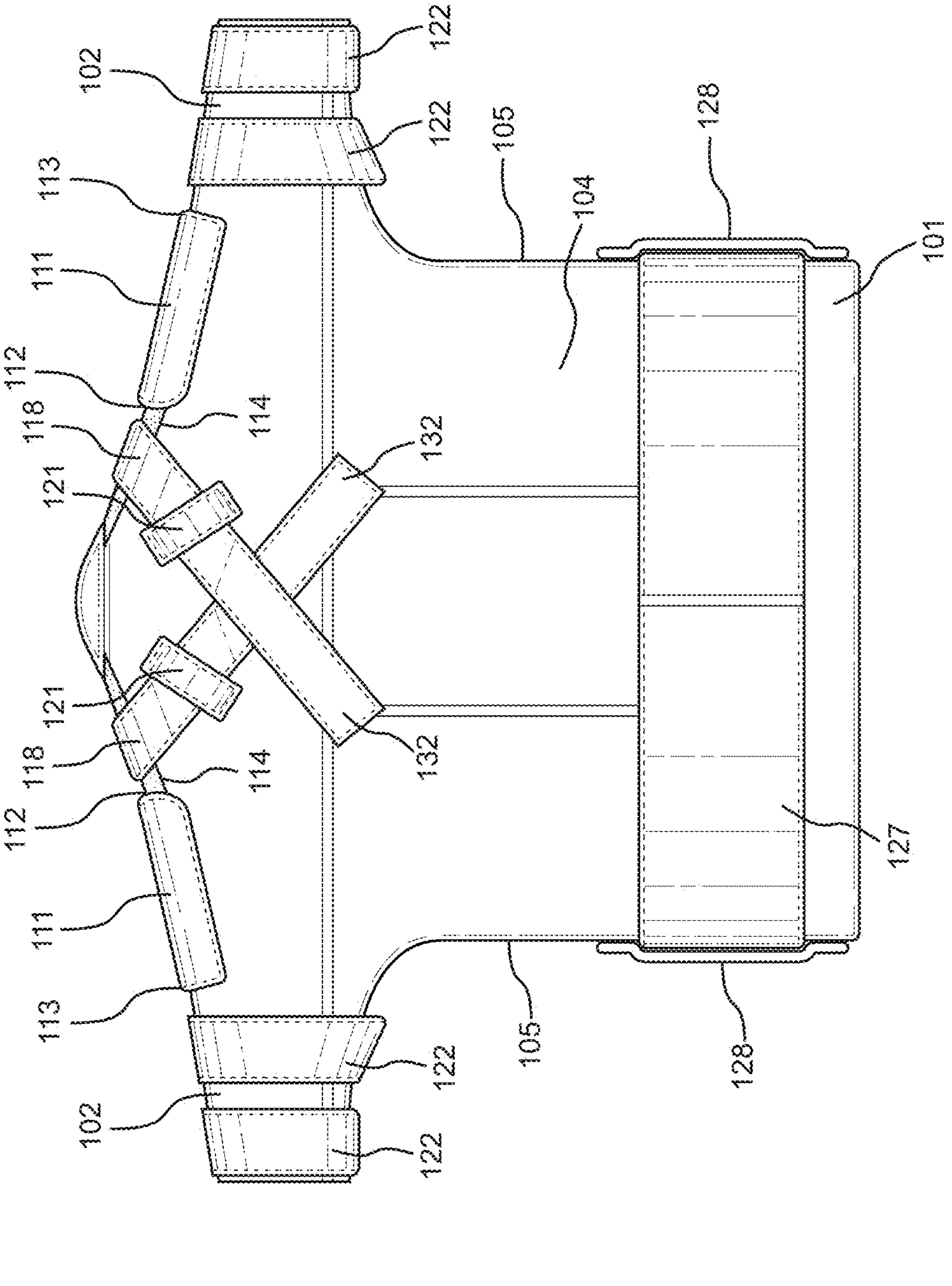
FIG. 2 shows a rear view of an embodiment of the inventive shoulder support apparatus with securing elements in their releasably connected state.

The figures referred to above are not necessarily drawn to scale and should be understood to present a representation of the invention, illustrative of the principles involved. Some features of the shoulder support apparatus depicted in the drawings may have been enlarged or distorted relative to others to facilitate explanation and understanding. The same reference numbers are used in the drawings for similar or identical components and features shown in various alternative embodiments. The shoulder support apparatus, as disclosed herein, can have configurations and components determined, in part, by the intended application and environment in which it is used.

DETAILED DESCRIPTION

The inventor surprisingly discovered an apparatus capable of supporting and stabilizing the shoulder which provides compressive force to the shoulder in an upward and inward fashion simultaneously. The inventive apparatus does not require the user to keep their arm in a sling and supports the shoulder through its full range of motion so as to reduce the pain associated with the movements of an injured or weakened shoulder. The compressive force afforded by the apparatus also provides a massaging, soothing effect to sore shoulders. The supporting elements disclosed herein can be adjusted to provide a desired amount of compressive force as well as desired range of motion. Thus, the elements can be adjusted to prevent the shoulder from engaging in a degree of motion that may cause pain, injury, or compromise the rehabilitation of the shoulder.

FIGS. 1-6 show a non-limiting embodiment of the apparatus comprising torso engaging body 101 having sleeves 102. Torso engaging body 101 is configured to receive the torso of user, similarly to a form-fitting shirt. Torso engaging body 101 has a pair of opposing front sides 103, rear side 104, and opposing lateral side portions 105. Opposing front sides 103 are releasably connected to one another by zipper 106. While the apparatus is depicted with zipper 106, it will be appreciated that opposing fronts sides 103 can be releasably connected by any suitable means, such as Velcro™, buttons, snaps, or a hook-and-loop connection. Torso engaging body 101 can be made of an elastic material, such as neoprene or neoprene that is laminated with a fabric on one or both of the inside and outside of torso engaging body 101. Other suitable materials for torso engaging body 101 include, without limitation, nylon, lycra, elastane, polyester, and combinations thereof. Without being limited to any particular theory or mechanism, fabricating torso engaging body 101 with an elastic material provides compressive force to the torso, arms and shoulders thereby enhancing the supportive, stabilizing effect of the securing elements disclosed herein.

Figure 5:
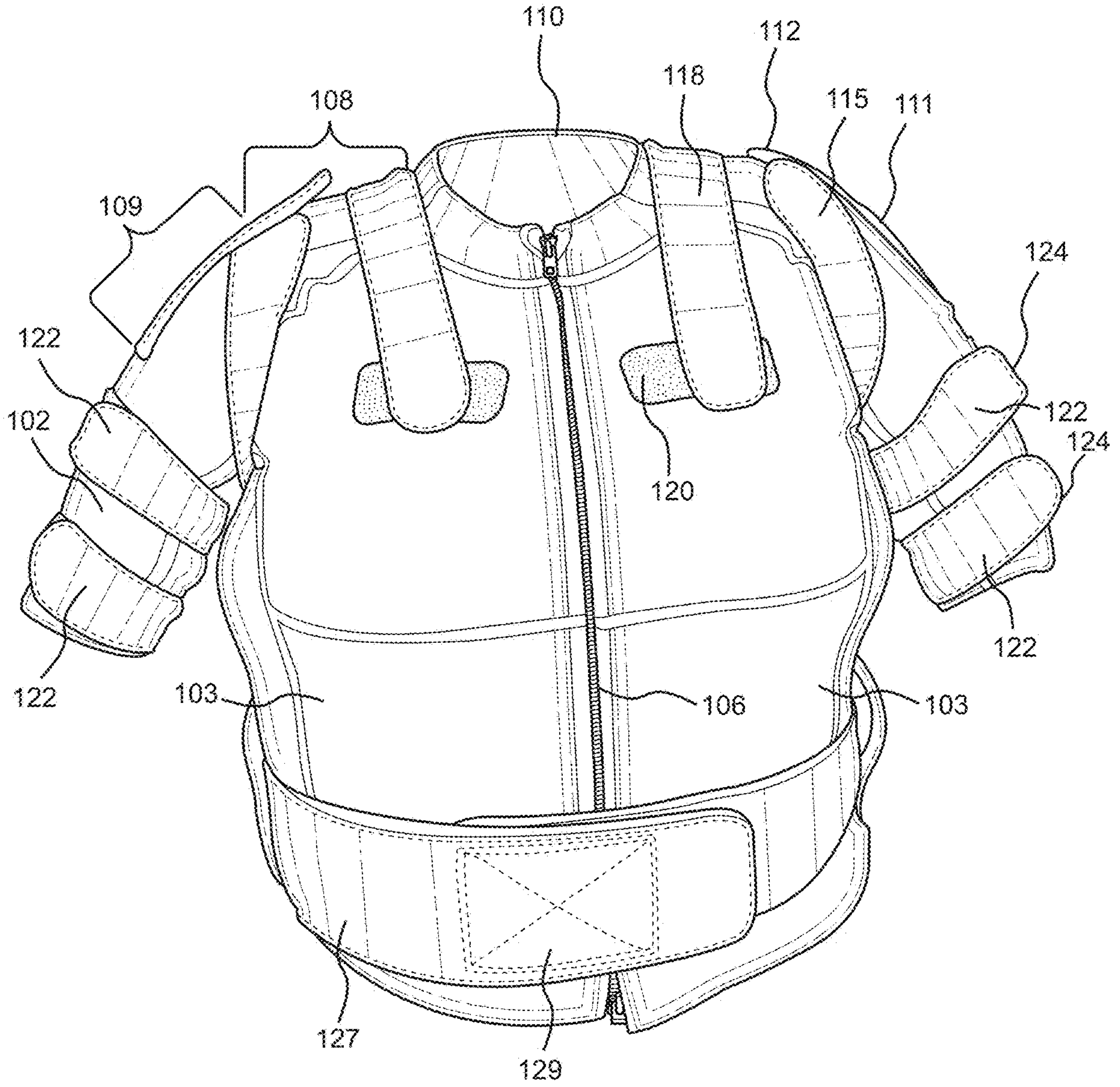
FIG. 5 shows a front perspective view of an embodiment of the inventive shoulder support apparatus, with securing elements in their releasably connected state, as worn by a user.
Figure 6:
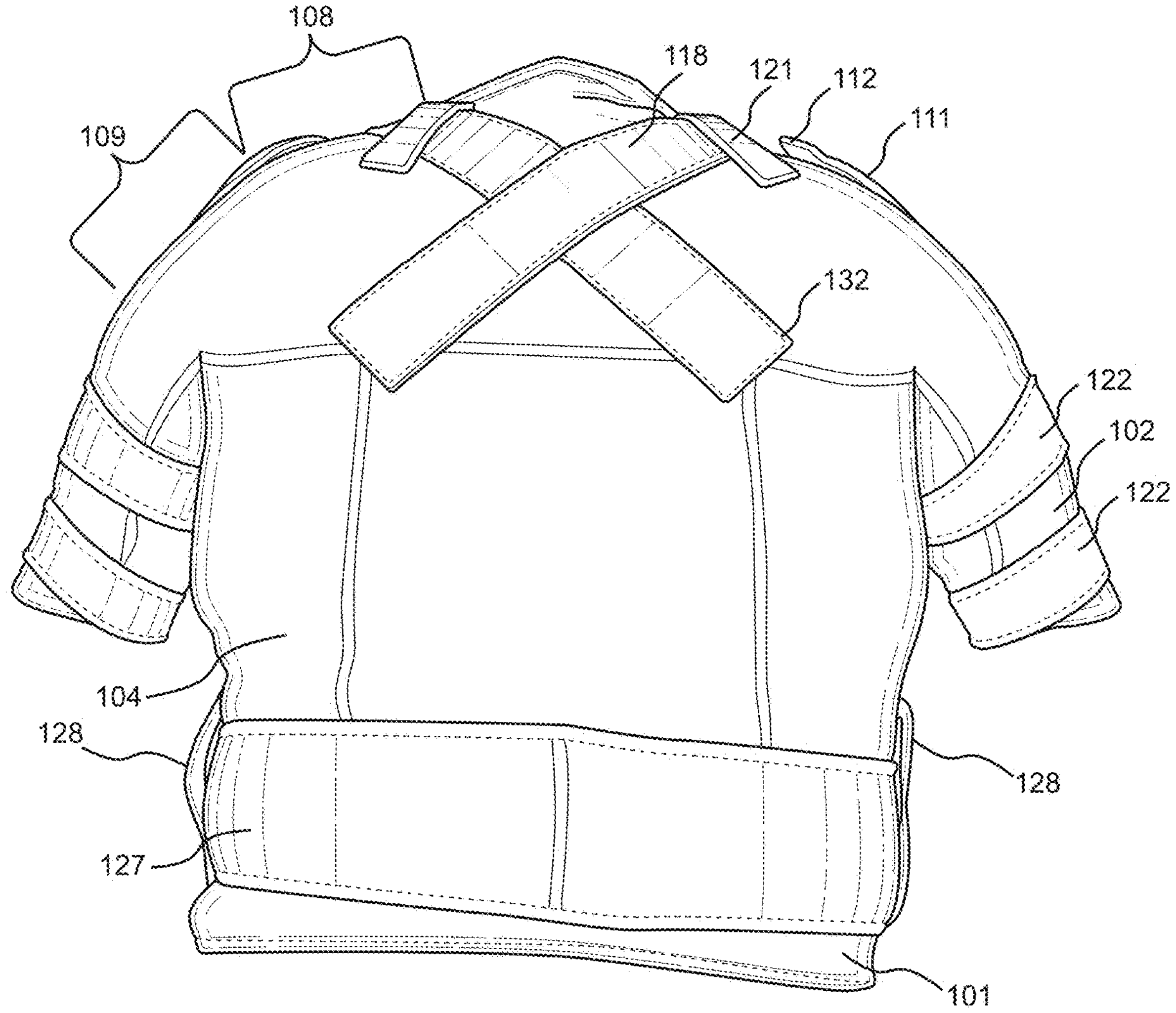
FIG. 6 shows a rear view of an embodiment of the inventive shoulder support apparatus, with securing elements in their releasably connected state, as worn by a user.

As shown in FIGS. 5 and 6, torso engaging body 101 further comprises upper shoulder portion 108 and lower shoulder portion 109. Upper shoulder portion 108 contacts the upper and middle trapezius of a user, while lower shoulder portion 109 contacts the front, medial and rear deltoids. Neck portion 110 forms an opening in torso engaging body 101 and is adapted to receive the neck of a user. Shoulder portions 108 and 109 can be formed from a continuous material with torso engaging body 101, and accordingly made of an elastic material as disclosed herein.

The inventive apparatus comprises one or more securing elements for providing compressive force against the shoulder, arm, waist, or combinations thereof. The inventive apparatus can have one or two of shoulder securing elements 111 and its associated connecting points. Shoulder securing elements 111 provide compressive force to pull the shoulder of a user upward inward toward the neck, head and torso. Shoulder securing elements 111 are adapted to connect to upper shoulder portions 108 by ends 112, and to at least one of lower shoulder portions 109 and sleeves 102 by ends 113. Thus, ends 113 can connect to lower shoulder portions 109, sleeves 102, or a combination of upper shoulder portions 109 and sleeves 102.

Shoulder securing elements 111 can be adapted to releasably connect to upper shoulder portions 108 by ends 112, and releasably connect to at least one of lower shoulder portions 109 and sleeves 102 by ends 113. In such embodiments, ends 112 and 113 can comprise, for example a releasable connection means, such as Velcro™, buttons, snaps, or zippers, it being understood that upper shoulder portions 108, lower shoulder portions 109, and sleeves 102 will have a mating connection means. In a preferred embodiment, ends 113 are fixed to at least one of sleeves 102 and lower shoulder portions 109, such as by sewing, while ends 112 are releasably connectable to upper shoulder portion 108 by connections 114, which can be Velcro™ patches sewn into upper shoulder portions 108.

The inventive apparatus can further comprise one or more shoulder securing elements 115 to provide compressive force to pull the shoulder of a user upward toward the upper and middle trapezius. Shoulder securing elements 115 are adapted to connect to upper shoulder portions 108 by ends 117, and to at least one of rear side 104 and laterals side portions 105 of torso engaging body 101 by ends 116. Shoulder securing elements 115 can be adapted to releasably connect to connections 114 on upper shoulder portions 108 by ends 117, and to releasably connect to at least one of rear side 104 and laterals side portions 105 of torso engaging body 101 by ends 116. Ends 116 and 117 can comprise any suitable releasable connection means including, without limitation, Velcro™, buttons, snaps, and zippers. It will be understood that connections 114 on upper shoulder portions 108 and at least one of rear side 104 and laterals side portions 105 of torso engaging body 101 will comprise a mating connection means suitable for the attachment of ends 116 and 117. For example, ends 117 and releasable connections 114 on upper shoulder portion 108 can be Velcro™. In a preferred embodiment, ends 116 are fixed to at least one of rear side 104 and laterals side portions 105 of torso engaging body 101, such as by sewing, while ends 117 comprise connections 107 which can be Velcro™ patches sewn into ends 117.

The inventive apparatus can further comprise one or more shoulder securing elements 118 to provide compressive, downward force on the upper and middle trapezius to further stabilize the shoulder. Shoulder securing elements 118 are adapted to connect to rear side 104 by ends 132, and to front sides 103 of torso engaging body 101 by ends 119. Ends 119 and 132 can be adapted to releasably connect to their respective connection points using any suitable connection means, including, without limitation, Velcro™, buttons, snaps, and zippers.

In some preferred embodiments, ends 132 are fixed to rear side 104 of torso engaging body 101 by sewing, for example, while ends 119 have sewn thereon Velcro™ patches 133 which are adapted to attach to connections 120 on front sides 103 of torso engaging body 101, it being understood that connections 120 will be mating Velcro™ patches sewn into torso engaging body 101. Shoulder securing elements 118 can cross over one another on rear surface 103 and be held in place by loops 121 to permit shoulder securing elements to slide through loops 121 to permit adjustment of shoulder securing elements 118.

The inventive apparatus can further comprise one or more arm securing elements 122 which are adapted to wrap around sleeves 102 and provide compressive force to stabilize and support the arm of a user, and prevent sleeves 102 from sliding up the arm. Arm securing elements 122 can releasably connect to sleeves 102 by ends 123 using a releasable connection means as disclosed herein. In a preferred embodiment, ends 123 are fixed to sleeves 102, by sewing for example. Arm securing elements 122 further include ends 124 having thereon releasable connections 125 so as to permit arm securing elements 122 to wrap around the arm of a user and releasably attach to connections 126 on sleeve 102. Connections 125 and 126 can be a releasable connection means as disclosed herein. Alternatively, arm securing elements 122 can have releasable connections on a middle portion on the planar side opposing connection 125 so as to permit arm securing elements 122 to wrap around the arm of a user and attach to the middle portion of arm securing element 122. In a preferred embodiment, connections 125 and 126 are Velcro™ patches wherein connections 125 are sewn onto ends 124 of arm securing elements 122 and connections 126 are sewn onto sleeves 102.

In some embodiments, the apparatus further comprises waist securing element 127 which functions to further secure torso engaging body 101 to the user and provides back support. Waist securing element 127 can be held in place by loops 128 which engage waist securing element 127 in a slidable relationship and permit the adjustment of waist securing element 127 around the waist of a user. Waist securing element 127 includes connections 129 and 130 on opposing sides of waist securing element. Connections 129 and 130 can be a releasable connection means, as disclosed herein, that permit waist securing element 127 to be adjusted around the waist of the user. In a preferred embodiment, connections 129 and 130 are Velcro™ mating patches sewn onto opposing sides of waist securing element 127.

Shoulder securing elements 111, 115 and 118, arm securing elements 122, and waist securing element 127 can be in the form of a strap, including a strap made of an elastic material, such as neoprene or neoprene that is laminated with a fabric on one or both sides. Other elastic materials include, but are not limited to, nylon, lycra, elastane, polyester, and combinations thereof. Fabricating apparatus' elements with an elastic material permits the elements to provide compressive force to support and stabilize the shoulders, arms and waist of a user. Moreover, the releasable connections of the elements permits them to be fully adjustable such that a user can achieve a desired level of support and stabilization.

Figure 3:
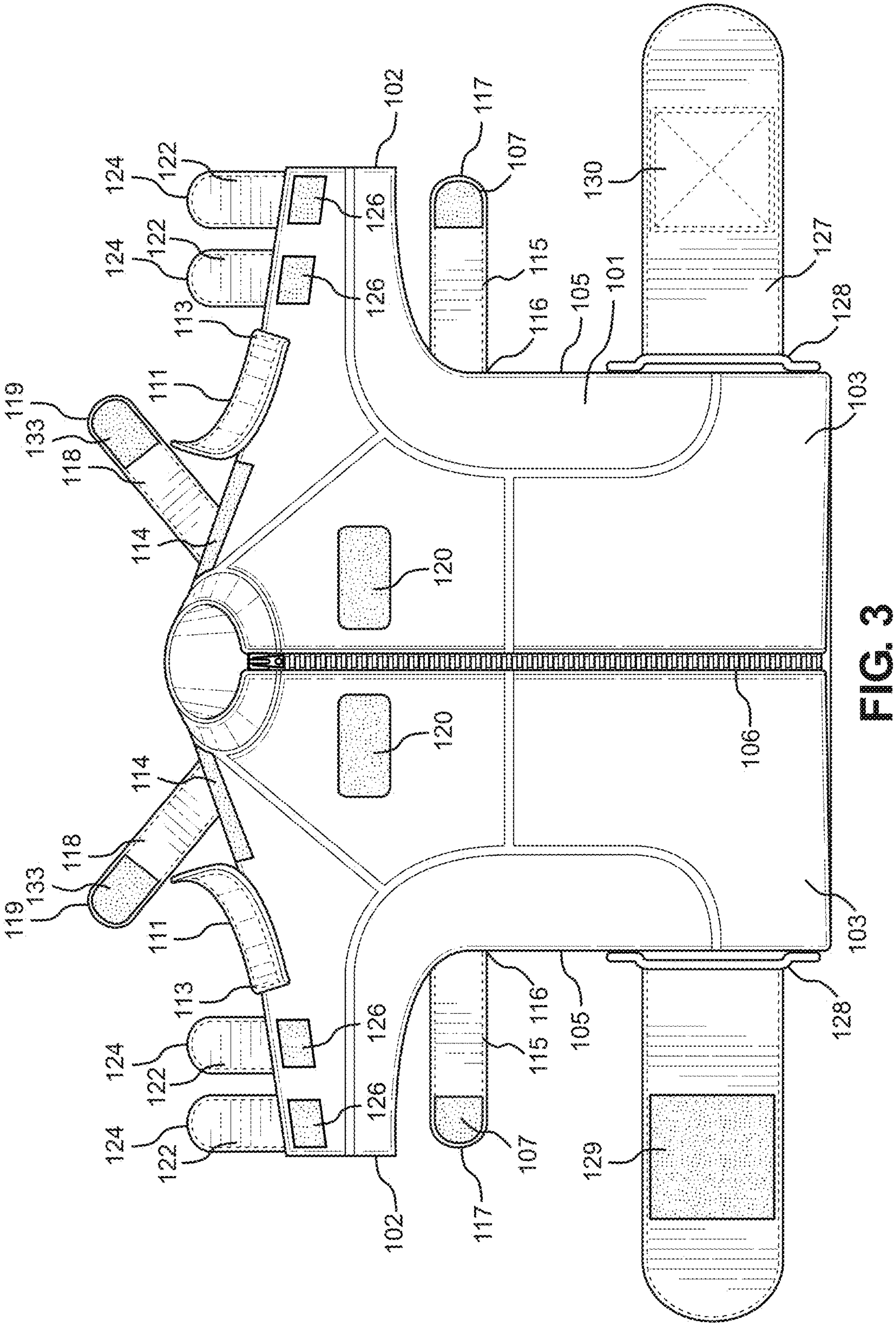
FIG. 3 shows a front view of an embodiment of the inventive shoulder support apparatus with securing elements in their released state.
Figure 4:
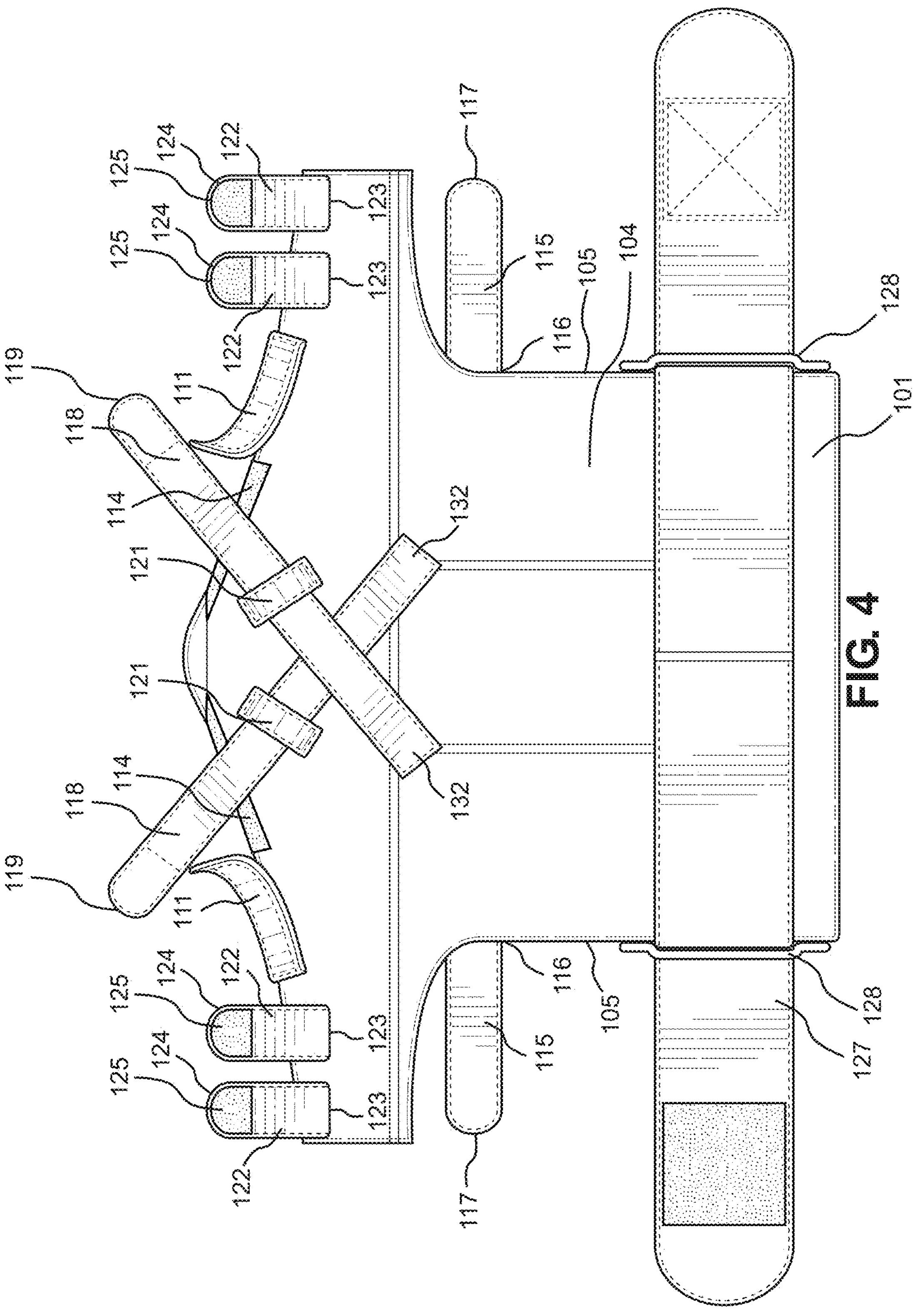
FIG. 4 shows a rear view of an embodiment of the inventive shoulder support apparatus with securing elements in their released state.

The inventive shoulder support apparatus can be practiced by a user separating shoulder securing elements 111, 115 and 118, arm securing elements 122, and waist securing element 127 from their respective connections such that the elements are in their elongated state as shown in FIG. 3. Zipper 106 is undone to separate front sides 103 from one another. The user then adorns the apparatus as a user would a button down shirt wherein the user places their arms through sleeves 102. The user then closes zipper 106 to join front sides 103. Arm securing elements 122 are then wrapped around the arm of the user from the back of the arm and connections 125 are attached to connection 126.

Shoulder securing elements 111 are then pulled upwards and toward the head and neck of the user and ends 112 are attached to connections 114. The user may elect to raise their arms out to the side before attaching ends 112 to connections 114 to increase the compressive force against the shoulder provided by shoulder securing elements 111. Shoulder securing elements 115 are then pulled forward and upward under the axilla of the user and ends 117 are attached to connections 114 thereby providing upward compressive force to support the user's shoulders and relieving the shoulders of the weight of the user's arms. Shoulder securing elements 119 are then pulled over the upper and middle trapezius of the user and ends 119 are attached to connections 120 on the chest of the user by connections 133. Waist securing element 127 is then wrapped around the waist of the user and connection 129 is attached to connection 130 to provide compressive force around the waist and lower back of the user.

While the inventive apparatus is depicted with a pair of each of shoulder securing elements 111, 115 and 118, it will be appreciated that the apparatus can be practiced with only one of each of these elements on either the right or left side of the apparatus, from the perspective of the user.

The invention claimed is:

1. A shoulder support apparatus, comprising:

a) a torso engaging body having (i) a sleeve, (ii) a shoulder portion having a lower shoulder portion and an upper shoulder portion, and (iii) a first front side and a second front side, wherein the first front side and the second front side are releasably connectable to one another by a zipper;

b) a first shoulder securing element having a first end and a second end, wherein (i) the first end of the first shoulder securing element is fixed to at least one of the lower shoulder portion and the sleeve, and (ii) the second end of the first shoulder securing element is adapted to releasably connect to the upper shoulder portion;

c) a second shoulder securing element having a first end and a second end, wherein (i) the first end of the second shoulder securing element is fixed to at least one of a back side of the torso engaging body and a lateral side of the torso engaging body, and (ii) the second end of the second shoulder securing element is adapted to releasably connect to the upper shoulder portion;

d) a pair of third shoulder securing elements each having a first end and a second end, wherein the first ends of the third shoulder securing elements are fixed to the back side of the torso engaging body and the second ends of the third shoulder securing elements are adapted to releasably connect to a front side of the torso engaging body, wherein the pair of third shoulder securing elements cross over one another on the back side of the torso engaging body e) at least one arm securing element that is adapted to wrap around an arm of a user while the user's arm occupies the sleeve, wherein the at least one arm securing element has a first end and a second end, wherein the first end of the at least one arm securing element is fixed to the sleeve and the second end of the at least one arm securing element is adapted to releasably connect to at least one of the first end of the at least one arm securing element and a middle portion of the at least one arm securing element; and f) a waist securing element adapted to encircle a waist of a user, wherein the waist securing element has a first end and a second end, wherein the first end of the waist securing element is adapted to releasably connect to the second end of the waist securing element.

* * * * *